United States Patent [19]

Leifeld et al.

[11] Patent Number: 5,130,559
[45] Date of Patent: Jul. 14, 1992

[54] METHOD AND APPARATUS FOR RECOGNIZING PARTICLE IMPURITIES IN TEXTILE FIBER

[75] Inventors: Ferdinand Leifeld, Kempen; Stefan Schlichter, Viersen; Norbert Tietgen, Munich, all of Fed. Rep. of Germany

[73] Assignee: Trützschler GmbH & Co. KG, Mönchen-Gladbach, Fed. Rep. of Germany

[21] Appl. No.: 568,873

[22] Filed: Aug. 17, 1990

[30] Foreign Application Priority Data

Aug. 26, 1989 [DE] Fed. Rep. of Germany ....... 3928279

[51] Int. Cl.$^5$ ............................................. G01N 21/88
[52] U.S. Cl. ..................................... 250/562; 250/572
[58] Field of Search ................. 250/562, 572; 356/237, 356/430, 431

[56] References Cited

U.S. PATENT DOCUMENTS

| 4,155,098 | 5/1979 | Roach et al. ......................... 250/562 |
| 4,652,125 | 3/1987 | Bowen et al. ......................... 250/562 |
| 4,692,799 | 9/1987 | Saitoh et al. ......................... 250/562 |
| 4,737,649 | 4/1988 | Naruse ................................. 250/562 |
| 4,739,176 | 4/1988 | Allen et al. . |

FOREIGN PATENT DOCUMENTS

| 226430 | 6/1987 | European Pat. Off. . |
| 1183718 | 12/1964 | Fed. Rep. of Germany . |
| 2700972 | 9/1979 | Fed. Rep. of Germany . |
| 3321261 | 10/1985 | Fed. Rep. of Germany . |
| 3436498 | 4/1986 | Fed. Rep. of Germany . |
| 3641816 | 6/1988 | Fed. Rep. of Germany . |
| 3027373 | 7/1988 | Fed. Rep. of Germany . |
| 3644535 | 7/1988 | Fed. Rep. of Germany . |
| 3703449 | 8/1988 | Fed. Rep. of Germany . |
| 3708188 | 9/1988 | Fed. Rep. of Germany . |
| 3734145 | 4/1989 | Fed. Rep. of Germany . |
| 62-93637 | 4/1987 | Japan . |
| 669401 | 3/1989 | Switzerland . |
| 2009395 | 6/1979 | United Kingdom . |
| 2093586 | 9/1982 | United Kingdom . |
| 2152660 | 8/1985 | United Kingdom . |

OTHER PUBLICATIONS

Bermbach et al "Zeilensensor überwacht Bewegte Objekte", Elektronik 24/Nov. 28, 1986, pp. 99–102.

Wulfhorst, et al "Erkennen von Störpartikeln im Vlies vom Baumwollfasern mit Hilfe der digitalen Bildverarbeitung", Melliand Textilberichte Dec. 1989, pp. 887–889.

Kaasjager "Kontrolle der Warenbahn mit elektronischer Bildanalyse", Melliand Textilberichte Jan. 1990, pp. 64–66.

Marguerre, "Neue optische Verfahren für die automatisierte Sichtprüfung", Messen Prüfen Automatisieren, May 1998, pp. 274–278.

Primary Examiner—David C. Nelms
Assistant Examiner—K. Shami
Attorney, Agent, or Firm—Spencer, Frank & Schneider

[57] ABSTRACT

A method of recognizing particle impurities in textile material includes the following steps: forming a thin fiber web; detecting each particle impurity by an electron-optical sensor; applying signals from the sensor to an image processing system; determining a specific characteristic for each particle impurity by an evaluating device forming part of the image processing system; classifying the particle impurities based on the specific characteristic by comparison with reference data; and counting the particle impurities.

25 Claims, 5 Drawing Sheets

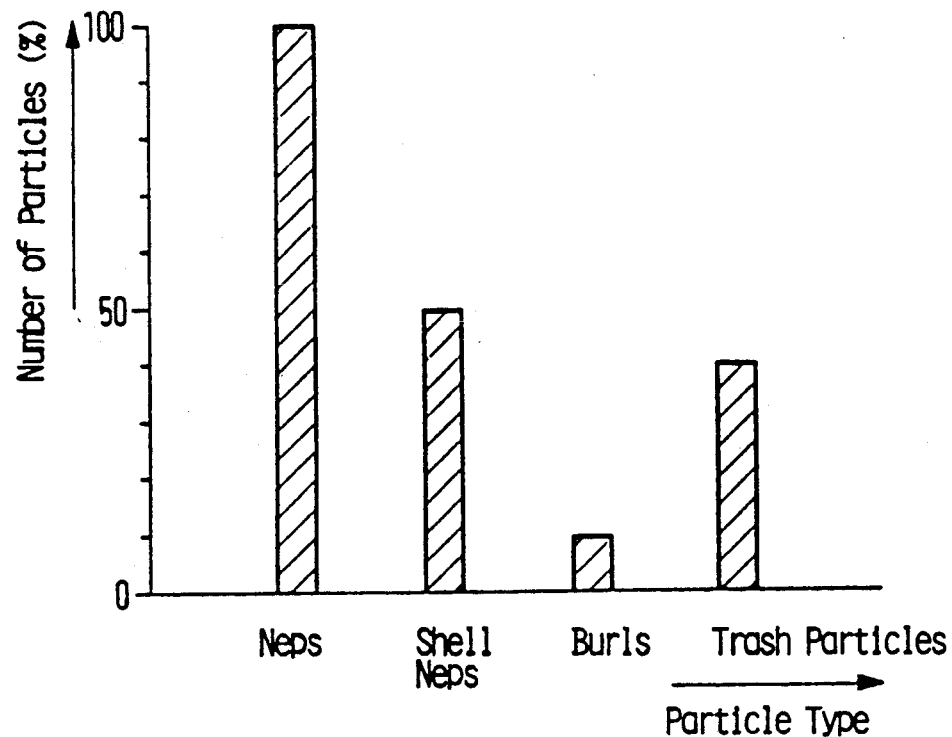

Fig. 9
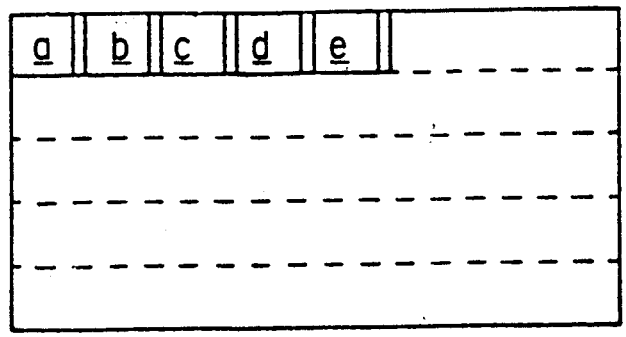
Fig. 10
 Burls (Fiber Knots > approx. 1 mm)
 Neps (Fiber Knots < approx. 1 m)
 Trash Particles, Leaf and Shell Fragments
 Shell Neps and Grain Shell Fragments
Fig. 11
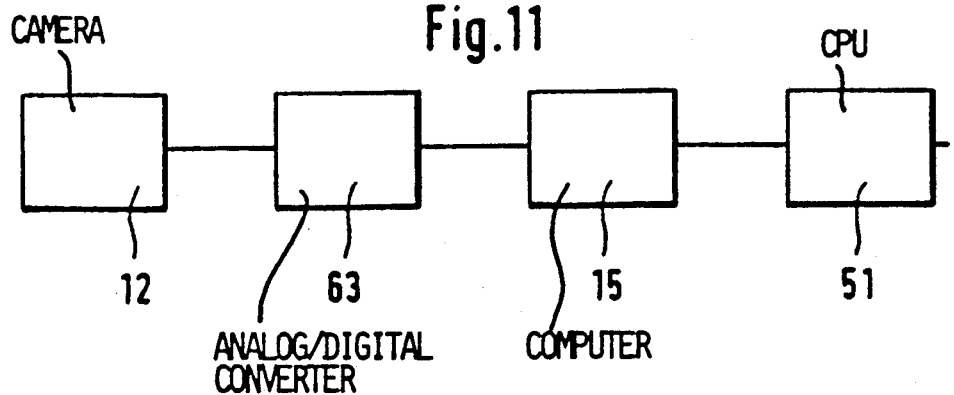

METHOD AND APPARATUS FOR RECOGNIZING PARTICLE IMPURITIES IN TEXTILE FIBER

CROSS REFERENCE TO RELATED APPLICATION

This application claims the priority of Federal Republic of Germany Application No. P 39 28 279.1 filed Aug. 26th, 1989, which is incorporated herein by reference.

BACKGROUND OF THE INVENTION

This invention relates to a method and an apparatus for recognizing particle impurities, such as trash fragments, neps, shell neps, burls and the like in textile fibers such as cotton, chemical fibers and the like. The determination of the degree of impurities (trash content) of the fiber is effected by electron-optical means: the fiber is scanned by a sensor and the measuring values are applied to an image processing device.

Neps are fiber knots smaller than approximately 1 mm, while shell neps are grain shell fragments which have grown-on fibers. Burls, on the other hand, are fiber knots that are greater than approximately 1 mm and trash particles are, for example, leaf and shell fragments. Elongated trash particles (bark, grass or stem fragments) form a special class (subclass), whose length/width ratio is large. These particle impurities are summarized in FIG. 10.

In a known process for cleaning and opening fiber to obtain fiber tufts, the fiber material passes through a feeding device and is thereafter submitted to a cleaning process. The degree of fiber impurity is determined during the supply of the fiber material to the cleaner.

For performing the known impurity detecting process, between a feeding device and an opening/cleaning device a measuring line (measuring section) is provided for the fiber material. The measuring line comprises a channel-like guide having a transparent plate which is illuminated by a lamp and a conveyor belt which serves for pressing the fiber layer in the channel against the transparent plate, whose distance from the conveyor belt is approximately 2–4 cm. The measuring line further comprises a camera which applies signals to a grey scale value comparator, a counter and a computer. This apparatus serves for improving the cleaning process performed by the cleaner which receives the fiber material. The fiber material which is discharged by the cleaning device is introduced to a carding machine or a roller card unit.

It is a disadvantage of the above-outlined process that the fiber tuft layer supplied to the cleaner is approximately 2–4 cm thick so that only impurities on the surface may be detected whereas those inside the material remain undetected. It is a further disadvantage of known processes that of the impurities determined on the surface in a reflecting light only a percent proportion in relation to the fibers can be summated. It is also a drawback that impurities such as neps, shell neps and burls which have a particularly adverse effect on the usual spinning processes cannot be detected.

SUMMARY OF THE INVENTION

It is an object of the invention to provide an improved method and apparatus of the above-outlined type from which the discussed disadvantages are eliminated and which, in particular, are capable of detecting particle impurities inside the fiber layer and further, a determination and a differentiated evaluation of trash particles, neps, shell neps and burls are possible.

This object and others to become apparent as the specification progresses, are accomplished by the invention, according to which, briefly stated, a thin fiber web is formed, then a sensor stepwise detects each individual particle impurity. An evaluating device determines specific characterizing magnitudes, for example, grey scale values for each individual particle. Based on the characteristic values the individual particles are classified, for example, according to type, shape and size and the individual particles are counted.

By providing a thin, light-transmitting fiber web (which has a weight of, for example, 5 g/m$^2$), particle impurities are detected both on the surface and inside the fiber web. According to the invention, the sensor stepwise detects each individual particle, for example, up to a magnitude of 0.1 mm. The sensor may be, for example, a camera which detects a certain zone of the fiber web and generates electric pulses which correspond to the detected image and which are applied to an electronic evaluating device. For each individual particle specific magnitudes are determined in the evaluating device, for example, based on a grey scale value analysis (identification as a particle impurity). Based on these magnitudes, the individual particle is classified by means of a comparison, for example, with predetermined stored data, particularly according to type, shape and size. Thereafter, the individual particles are counted so that, for example, a type classification (number of particles per type) or a size classification (number of particles for a certain size) is possible.

By means of the process according to the invention, the particle impurities are detected even in the inside of the fiber layer and thus all the particle impurities in the entire fiber layer are accounted for. In addition to trash particles, other impurities such as neps, shell neps and burls are detected and eventually all particle impurities are classified in accordance with certain criteria, such as type, shape and size.

According to further feature of the invention, the shell neps are detected in transmitted light and at least two different grey scale values are evaluated for the recognition of the shell neps. Preferably, the shell neps are determined by comparing the measuring results in transmitted light and reflected light.

The novel apparatus for practicing the above-outlined method according to the invention has a measuring line which comprises a sensor assembly including a camera, for example, a diode-line camera or a two-dimensional camera, an electronic evaluating device (image processing unit), a classifying device, a counter and a computer.

According to a further feature of the invention, a switching device is provided for activating either a light source from which light is passed through the textile material or a light source which generates light that is reflected from the fiber material. According to another feature of the invention, the electronic evaluating device includes a comparator for comparing electric pulses generated with transmitted light with those generated with reflected light. Further, the evaluating device preferably includes a grey scale value filter. According to a further feature of the invention the computer is connected with a quality detecting device involved in the carding process, such as a card information system.

BRIEF DESCRIPTION OF THE DRAWING

FIG. 7 is a bar diagram showing classification of particle impurities.

FIG. 8 is a table showing grey scale value ranges of a fiber web image.

FIG. 9 illustrates a schematic combination of the total image formed from stepwise taken individual images.

FIG. 10 is a schematic illustration, with legends, of various particle impurities.

FIG. 11 is a block diagram of circuit components of the invention.

DESCRIPTION OF THE PREFERRED EMBODIMENTS

Figure 1:
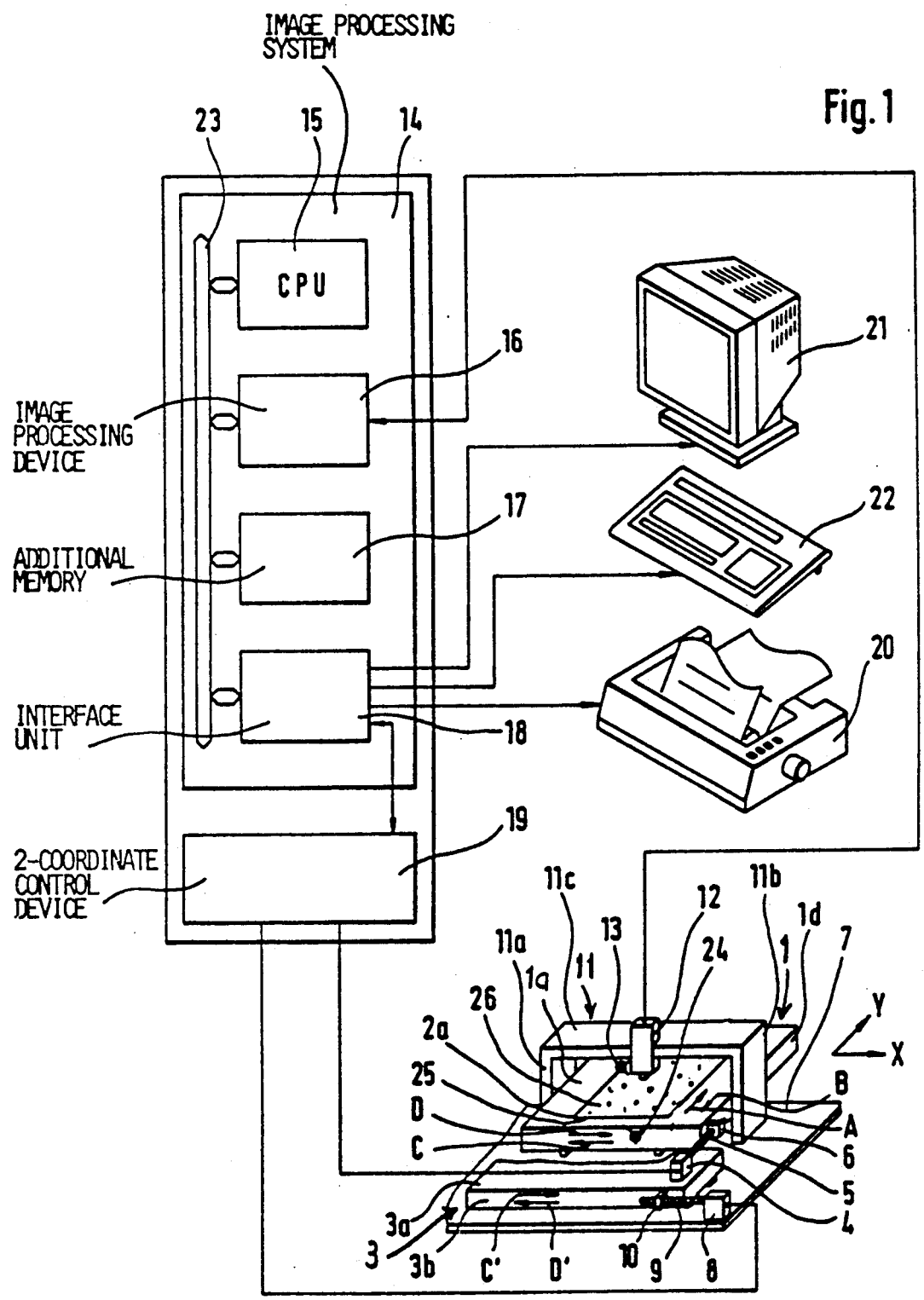
FIG. 1 is a schematic perspective view, block diagram, of a preferred embodiment of the invention.

Turning to FIG. 1, there is illustrated therein a positioning device including a table 1 movable in the direction of the coordinates X and Y of a two-coordinate system. The table 1 has an upper cover face 1a, a glass plate 2a positioned thereon, a lower cover plate (not visible) and a second glass plate (also not visible) positioned on the lower cover plate. An illuminating device 24 is provided underneath the glass plate 2a. The fiber web (specimen) 25 is positioned on the upper glass plate 2a. The particle impurities in the fiber web 25 are designated at 26. Externally of the table 1 there is arranged a displaceable holding plate 3 on which a stepping motor 4 is mounted. The rotatable shaft of the motor 4 is a threaded spindle 5 which cooperates with a nut 6 fixed to a lateral face 1d of the table 1. Upon rotation of the threaded spindle 5 the table 1 is displaced in the direction of arrows A, B. Externally of the table 1 and the holding plate 3 there is provided a stationary support plate 7 on which a stepping motor 8 is mounted. The shaft of the stepping motor 8 is a threaded spindle 9 which cooperates with a nut 10 which, in turn, is secured to the lateral face 3b of the holding plate 3. Upon rotation of the spindle 9 the holding plate 3 is moved in the direction of arrows C', D' and, at the same time, with the intermediary of a mechanical connection, the table 1 is displaced in the direction of the arrows C, D. The table 1 is straddled by an inverted U-shaped yoke 11 whose vertical legs 11a, 11b are secured on the support plate 7 and whose transverse head 11c carries a camera 12 (for example, a diode-row camera) and an illuminating device 13. A digital image processing in which the image is divided into individual pixels is particularly adapted for practicing the invention. In addition to the stepping motors 4 and 8, limit switches (not shown) are provided which permit the assumption of a zero position.

The apparatus further includes an image processing system 14 having a central processing unit 15 such as a microprocessor, an image processing device 16, an additional memory 17 and an interface unit 18. A two-coordinate control device 19 is connected to the interface unit 18 and to the stepping motors 4 and 8. Further, the image processing device 16 is connected with the camera 12 to receive signals therefrom. It is noted that a plurality of cameras 12 may be connected with the image processing device 16. The interface unit 18 is further connected with a printer 20, a screen terminal 21 and a keyboard 22. A data bus associated with the components 15-18 is designated at 23.

The apparatus illustrated in FIG. 1 which may be used, for example, as a laboratory equipment, comprises the image processing system 14 (encompassing the additional memory 17 and the interface unit 18), the terminal 21, the light source 24 for providing throughgoing light and a light source 13 for providing reflected light. The fiber web 25 may be positioned between the thin transparent plates. The camera 12 mounted on the transverse head 11c scans stepwise a programmable measuring range. The trash particles 26 and neps detected during this process are classified. The terminal 21 and the printer 20 may display the measuring results and size distributions (histograms). During examination in throughgoing light all opaque particles, for example, trash particles 26 or shell neps are detected and classified by size. During measurements taken in reflected light the neps and burls are highlighted by the illuminating and image receiving optics as locally limited, light zones. These zones are recognized as neps by the image processing system 14. The recognized neps and burls are also classified by size. The duration of the examination for detecting trash particles 26 and shell neps may last, for example, 3-20 minutes. The particles visible in transmitted light are detected up to a minimum size of approximately 0.1 mm diameter, the maximum size may reach 60 mm. The particles evaluated in reflected light are recognized as neps having a minimum diameter from approximately 0.1 mm. The maximum size of the burls is approximately 2 mm.

Figure 2:
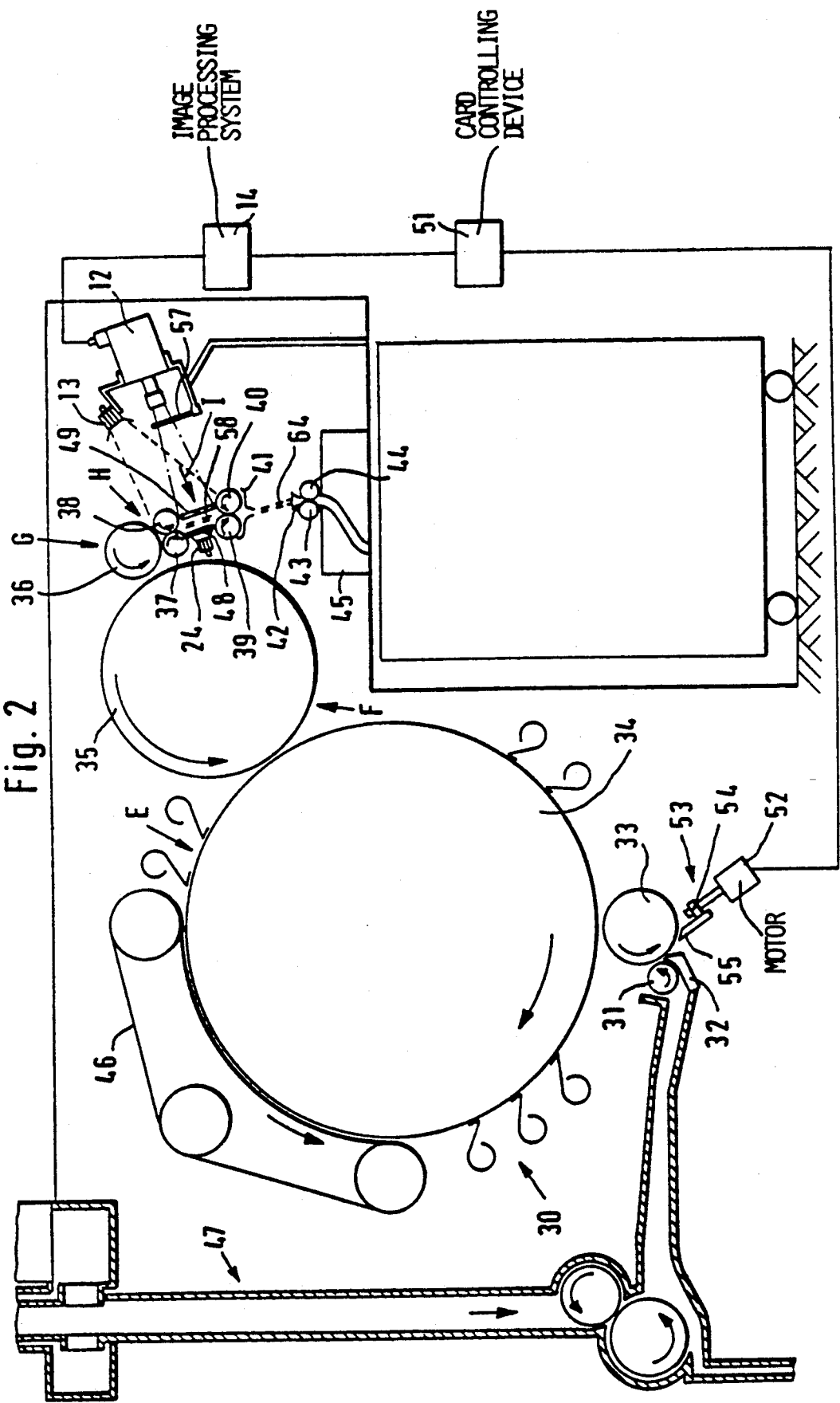
FIG. 2 is a schematic side elevational view of a carding machine, incorporating the invention.

Turning now to FIG. 2, there is illustrated therein a carding machine 30 which has a feed roller 31, a feed table 32, a licker-in 33, a main carding cylinder 34, a doffer 35, a stripping roll 36, crushing rolls 37, 38, transport rolls 39, 40, a web guiding element 41, a sliver trumpet 42, calender rolls 43, 44, a sliver coiler 45 and travelling flats 46. The carding machine is supplied with a fiber batt (not shown) from a fiber tuft feeder 47.

Between the crushing rolls 37, 38 which discharge a thin fiber web 58 and the transport rolls 39, 40 which receive and further advance the fiber web 58 there are provided two transparent stationary plates 48, 49 in a channel-like arrangement which constitute a measuring section 50 and between which the fiber web 58 runs. The plates 48, 49 are spaced approximately 2-10 cm from one another. The transparent (or at least translucent) plates 48, 49 at the same time screen interfering air streams which could tear apart the thin fiber web 58, particularly at high-speed runs. The sliver discharged by the rolls 39, 40 is designated at 64.

The apparatus for recognizing particle impurities in the fiber web 58 which passes through the measuring section 50 includes a camera 12 and an image processing system 14 (FIG. 1) which includes a grey scale value comparator, a counter and a computer. The image processing device 14 applies signals to a control device 51, for example, a machine control of the card 30. The control device 51 is connected with a regulatable drive motor 52 which varies the distance of a mote knife 55 from the licker-in 33 by means of a drive arrangement 53. It is also feasible to regulate in a similar manner an adjustable waste guide element or drives for various rotating rolls of the carding machine. In this manner, an on-line recognition and detection of particle impurities coupled with a regulation of the separation of the particles is effected. When predetermined limit values are exceeded, which are stored in the memory 17, the carding machine may be stopped by means of the control device 51 or a warning signal may be generated. The camera 12 may have an optical filter 57. Further, for generating reflected light, a light source 13 is arranged on the side of the camera, and for generating through-going light, a light source 24 is arranged on the transparent plate 48 on its side opposite the camera 12.

The following zones in the carding machine 30 may be used as measuring locations for the fiber web: the fiber layer (arrow E) on the carding cylinder 34, the fiber layer (arrow F) on the doffer 35, the fiber layer (arrow G) on the stripping roll 36, the fiber web (arrow H) between the stripping roll 36 and the crushing rolls 37, 38, or the fiber web (arrow I) between the crushing rolls 37, 38 and the conveying rolls 39, 40. The particle impurities in the fiber web are recognizable only in reflected light on the carding cylinder 34, the doffer 35 and the stripping roll 36, for example, neps in case of chemical fibers, while the particle impurities between the stripping roll 36 and the crushing rolls 37, 38 or between the crushing rolls 37, 38 and the conveying rolls 39, 40 may be recognized in either transmitted light or reflected light. Expediently, the web is scanned along the extire axial length of the roll which supports the web. In this manner a determined impurity distribution may be indicative of a localized clothing defect in the carding machine.

Figure 3:
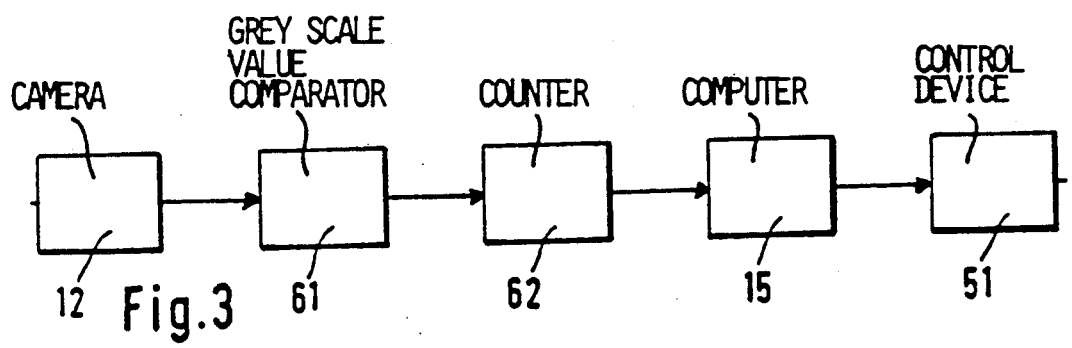
FIG. 3 is a block diagram of a circuit component of the preferred embodiment.

As shown in FIG. 3, the camera 12, the grey scale value comparator 61, the counter 62, the computer 15 and the control device 51 are connected in series. The classification and counting of the particle impurities are effected by corresponding computer softwares.

For the classification of the particles, the following considerations apply:
1) Type
   a) nep:
      recognition in reflected light after grey scale value filtering.
   b) trash particles:
      recognition in transmitted light after grey scale value filtering.
   c) elongated trash particles (bark, grass):
      this class forms a special class of trash particles.
   d) shell neps:
      either comparison in transmitted light (the core will become visible) and reflected light (the fibers of the neps will become visible),
      or only in reflected light:
      dark core (high grey scale stage), lighter fiber environment, as in case of a nep (low grey scale stage).

In addition to the described methods of recognition a)–d), grey scale value operations, edge detections or the like may be used for a better differentiation of the particles.
2) Size:
   the surface of the particles is determined in square millimeters (minimum diameter size is 0.1 mm).

Figure 4:
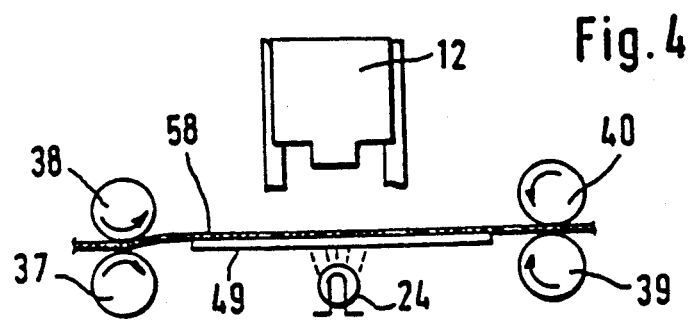
FIG. 4 is a schematic side elevational view of a component of the preferred embodiment.

FIG. 4 shows a glass plate 49 which is situated between the crushing rolls 37, 38 and the conveying rolls 39, 40 and over which the fiber web 58 runs. Above the glass plate 49 there is situated the camera 12 and underneath the glass plate 49 there is arranged the light source 24 for emitting light for passing through the web 58. The direction of rotation of the crushing rolls 37, 38 and the conveying rolls 39, 40 is indicated by respective arrows drawn therein.

Figure 5:
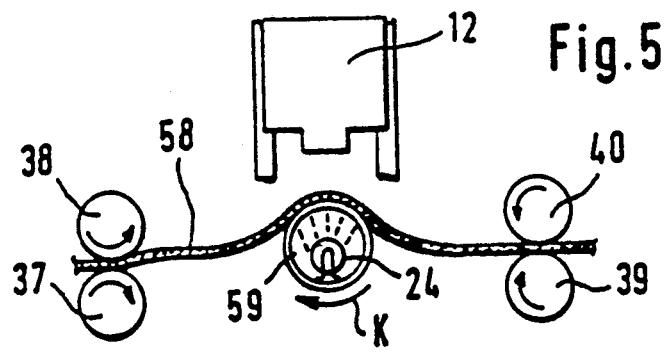
FIGS. 5 and 6 are schematic side elevational views of two variants of the arrangement shown in FIG. 4.

Turning to FIG. 5, between the crushing rolls 37, 38 and the conveying rolls 39, 40 there is arranged a roll 59 oriented axially parallel to the rolls 37–40 and rotating in the direction of the arrow K. The roll 59 has a transparent (glass) wall, over which the fiber web 58 runs. The circumferential speed of the roll 59 is expediently the same as the running speed of the fiber web 58, so that no relative motion (and thus friction) between roll and web is generated. The light source 24 is arranged inside the roll 59.

Figure 6:
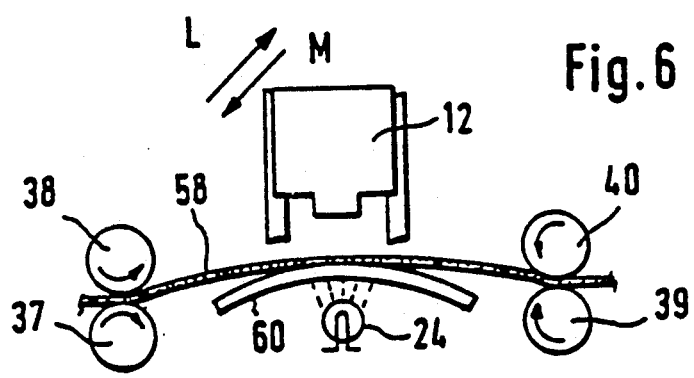

FIG. 6 shows an embodiment which is similar to that of FIG. 3, except that as a web support a convex glass plate 60 is provided over which the fiber web 58 slides and which ensures an improved web guidance when contacting the fiber web. The fiber web 58 is in contact with the glass plate 60 only with one part thereof. The upper crest point of the roll 59 and the glass plate 60 are expediently above the connecting line between the nip of the crushing rolls 37, 38 and the nip of the conveying rolls 39, 40. The arrows L and M indicate the direction in which the camera 12 may move.

FIG. 7 illustrates an exemplary bar graph showing a type classification where the particle proportions are given in percent relative to the particle type.

FIG. 8 shows in tabular form the grey scale value ranges of a web image wherein certain web elements (particle impurities and useful fibers) in each instance have been assigned particular grey scale values.

FIG. 9 shows that the image portions a–e of the individual takes is smaller than the entire specimen so that the summarized result in obtained by means of overlapping juxtaposition of several specimens.

FIG. 10 pictorially summarizes the four types of principal particle impurities (as described earlier in the Background of the Invention) intended to be detected by the method and apparatus according to the invention.

As shown in FIG. 11, the camera 12 is connected to an analog/digital converter 63 and the computer 15. The counting of the particle impurities is effected with the aid of a software in the computer 15. The analog/-digital converter 63 converts the sensor signal into a plurality of grey scale stages, for example, 200-300 in number. Expediently, the device illustrated in FIG. 2 has a CCD two-dimensional camcra 12. Preferably, the two-dimensional camera 12 has a device for a short-time illumination (exposure) to avoid at the carding machine 30 a blurred image due to motion, and thus the image is quasi-"frozen".

It will be understood that the above description of the present invention is susceptible to various modifications, changes and adaptations, and the same are intended to be comprehended within the meaning and range of equivalents of the appended claims.

What is claimed is:

1. A method of recognizing particle impurities in textile material, including the following steps:
   (a) forming a thin fiber web;
   (b) passing a first light beam through the web;
   (c) reflecting a second light beam from the web;
   (d) positioning a single type of electron-optical sensor such as to receive the transmitted light and the reflected light;
   (e) detecting each particle impurity by the electron-optical sensor;

(f) applying signals from the sensor to an image processing system;

(g) determining a specific characteristic for each particle impurity by an evaluating device forming part of the image processing system;

(h) classifying the particle impurities based on the specific characteristic by comparison with reference data; and (i) counting the particle impurities.

2. A method as defined in claim 1, wherein said specific characteristic is a grey scale value.

3. A method as defined in claim 1, wherein the classifying step includes classifying according to type, shape and size.

4. A method as defined in claim 1, further comprising the step of moving the sensor and the fiber web relative to one another.

5. A method as defined in claim 1, further comprising the step of stepwise moving the sensor in a programmable measuring range.

6. A method as defined in claim 1, wherein step (g) includes the step of evaluating at least two different grey scale values.

7. A method as defined in claim 1, wherein step (g) includes the step of comparing measuring results obtained from detection with light passed through the web with measuring results obtained from detection with light reflected by the web.

8. An apparatus for recognizing particle impurities in textile material, comprising (a) a single-type of electron-optical sensor means including a camera for being aimed at the textile material and to generate signals representing an image of the fiber material;

(b) a support means for supporting the fiber material in an effective range of the camera; said support means having opposite first and second sides; said camera being disposed at said first side;

(c) a first light source supported at said first side for providing the camera with light reflected by the fiber material;

(d) a second light source supported at said second side for providing the camera with light passing through the fiber material;

(e) an electronic image processing device connected to the camera for determining a specific characteristic for each particle impurity detected by the camera;

(f) a classifying device connected to the image processing device for classifying particle impurities based on the specific characteristic;

(g) a counter operatively connected to said camera for counting the particle impurities detected by the camera; and (h) a computer operatively connected to the camera, the image processing device, the classifying device and the counter.

9. An apparatus as defined in claim 8, wherein said support means is transparent; further comprising a switching means for activating a selected one of said first and second light sources.

10. An apparatus as defined in claim 9, wherein said image processing device includes a comparator for comparing signals generated by the camera in light traversing the fiber material with signals generated by the camera in light reflected by the fiber material.

11. An apparatus as defined in claim 8, wherein said image processing device includes a grey scale value filter.

12. An apparatus as defined in claim 8, wherein the classifying device includes means for classifying particle impurities detected by the camera by one of type and size.

13. An apparatus as defined in claim 8, further comprising a memory forming part of said classifying device.

14. An apparatus as defined in claim 8, wherein said support means comprises a table for receiving a specimen of the fiber material and means for moving the table in a two-coordinate system; and control means operatively connected with the computer and with the means for moving the table in the two-coordinate system.

15. An apparatus as defined in claim 8, wherein said support means comprises an at least translucent support arranged for supporting the fiber material in an effective range of the camera.

16. An apparatus as defined in claim 15, wherein the support has a convex supporting face.

17. An apparatus as defined in claim 16, wherein said support comprises a roll having a translucent or transparent cylindrical shell.

18. An apparatus as defined in claim 8, in combination with a carding machine having a plurality of clothed rolls; said camera being directed to fiber material being processed by said carding machine.

19. An apparatus as defined in claim 18, wherein the quantity of particle impurities is determinable along the axial length of said one clothed roll.

20. An apparatus as defined in claim 8, in combination with a carding machine having an outlet roll pair discharging a fiber web; said camera being directed to said fiber web.

21. An apparatus as defined in claim 8, in combination with a carding machine; further comprising an impurity separating means for removing particle impurities from the fiber material supported in the carding machine; a setting means for controlling the impurity separating means to alter a degree of separation of particle impurities from the fiber material; a control device connected to said setting means; said computer being connected to said control device for varying the degree of separation as a function of an extent of impurities detected by the apparatus.

22. An apparatus as defined in claim 21, wherein said impurity separating means comprises an adjustable mote knife.

23. An apparatus as defined in claim 8, in combination with a fiber web forming machine; said camera being directed to the fiber web during manufacture by the machine; said computer being connected with said fiber web forming machine for generating a warning or machine shutoff signal if a limit value for particle impurities in the fiber web is exceeded.

24. An apparatus as defined in claim 8, wherein said camera is a two-dimensional CCD camera.

25. An apparatus as defined in claim 24, wherein the two-dimensional camera includes a short-period exposure arrangement.

* * * * *